United States Patent
Snutch et al.

(10) Patent No.: US 6,294,533 B1
(45) Date of Patent: *Sep. 25, 2001

(54) CALCIUM CHANNEL BLOCKERS

(75) Inventors: Terrance Preston Snutch, Vancouver; Gerald Werner Zamponi, Calgary, both of (CA)

(73) Assignee: NeuorMed Technologies, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/401,699

(22) Filed: Sep. 23, 1999

Related U.S. Application Data (63) Continuation-in-part of application No. 09/107,037, filed on Jun. 30, 1998, now Pat. No. 6,011,035.

(51) Int. Cl.⁷ ...................... A61K 31/535; A61K 31/495; A61K 31/445

(52) U.S. Cl. ...................... 514/231.2; 514/255; 514/315

(58) Field of Search .............................. 514/231.2, 255, 514/315

(56) References Cited

U.S. PATENT DOCUMENTS

| | | | |
|---|---|---|---|
| 3,288,795 | 11/1966 | Irikura et al. | 260/268 |
| 4,188,485 | 2/1980 | Kukla | 546/202 |
| 4,918,073 | 4/1990 | Ruger et al. | 514/255 |
| 5,386,025 | 1/1995 | Jay et al. | 536/23.5 |
| 5,428,038 | 6/1995 | Chatterjee et al. | 514/253 |
| 5,623,051 | 4/1997 | Catterall et al. | 530/324 |
| 5,646,149 | 7/1997 | Hellberg et al. | 514/253 |
| 5,703,071 | 12/1997 | Itoh et al. | 514/218 |
| 6,011,035 | * 1/2000 | Snutch et al. | 514/231.5 |

FOREIGN PATENT DOCUMENTS

| | | |
|---|---|---|
| 0 187 524 | 7/1986 | (EP) . |
| 0 458 387 | 11/1991 | (EP) . |
| 504 202 | 1/1983 | (ES) . |
| 514 167 | 4/1983 | (ES) . |
| 1 513 883 | 6/1978 | (GB) . |
| WO 99 15129 | 4/1999 | (WO) . |
| WO 99 25686 | 5/1999 | (WO) . |

OTHER PUBLICATIONS

Cohan et al., "Depolarization–Induced Presynaptic Calcium Accumulation May Occur by an N–Type Channel that is Blocked by Flunarizine," *Annals of the New York Academy of Sciences* (1991) 635:397–399.

Database WPI Week 9711, Derwent Publications Ltd., London, GB; Abstract JP09 003067, XP002133055 (Hisamitsu Pharm Co Ltd.) Jan. 7, 1997.

Dhainaut et al., "New Triazine Derivatives as Potent Modulators of Multidrug Resistance," *J. Med Chem* (1992) 35:2481–2496.

Estep et al., "Synthesis and Structure–Activity Relationships of 6–Heterocyclic–Substituted Purines as Inactivation Modifiers of Cardiac Sodium Channels," *J. Med Chem* (1995) 38:2582–2595.

Glamkowski et al., "Synthesis of 3–(4–Acylaminopiperazin–1–ylalkyl) Indoles as Potential Antihypertensive Agents," *J Med Chem* (1977) 20(11):1485–1489.

Lehmann et al., "Zur Struktur und Pharmakologies γ–lactonverbruckter Diphenylalkylamine," *Arch Pharm* (1988) 321:807–812.

Miyano et al., "The Synthesis and Antilipidperoxidation Activity of 4,4–diarylbutylamines and 4,4–diarylbutanamides," *Chem Pharm Bull* (1990) 38(6):1570–1574.

Ohtaka et al., "Benzylpiperazine Derivatives. IV. Synthesis and Cerebral Vasodilating Activities of 1–Benzyl–4–diphenylmethyl–piperazine Derivatives," *Chem Pharm Bull* (1987) 35(8):3270–3275.

(List continued on next page.)

*Primary Examiner*—Raymond Henley, III
(74) *Attorney, Agent, or Firm*—Morrison & Foerster (57) ABSTRACT

Compounds of the formula

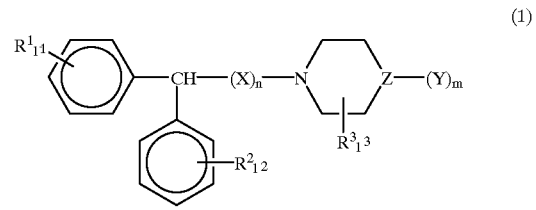

wherein m is 0, 1 or 2;

wherein when m is O, Z is O, when m is 1, Z is N, and when m is 2, Z is C;

Y is H, OH, $NH_2$, or an organic moiety of 1–20C, optionally additionally containing 1–8 heteaoms selected from te group consisting of N, P, O, S and halo;

each $1^1$ and 2 is independently 0–5;

$1^3$ is 0 or 1;

each of $R^1$, $R^2$ and $R^3$ is independently alkyl (1–6C), aryl (6–10C) or arylalkyl (7–16C) optionally containing 14 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1-4C) or alkyl (1-6C);

n is 0 or 1;

X is a linker, with the proviso that Y is not a tropolone, a coumarin, or an antioxidant containing an aromatic group and with the further proviso that if 13 is 0, neither R' nor $R^2$ can represent F in the para position; and are useful as calcium channel blockers. Libraries of these compounds can also be used to identify antagonists for other targets.

26 Claims, 3 Drawing Sheets

OTHER PUBLICATIONS

Ohtaka et al., "Benzylpiperazine Derivatives. V. Quantitative Structure–Activity Relationship of 1–Benzyl–4–diphenylmethylpiperazine Derivatives for Cerebral Vasodilating Activity," *Chem Pharm Bull* (1987) 35(10):4117–4123.

Prasad et al., "Potential Antihypertensive Agents. II. Unsymmetrically 1.4–disubstituted Piperazines,"*J Med Chem* (1968) 11(6):1144–1150.

Tytgat et al., "Flunarizine Inhibits a High–threshold Inactivating Calcium Channel (N–type) in Isolated Hippocampal Neurons," *Brain Research* (1991) 549:112–117.

Uneyama et al., "Non–L–type Actions of Organic $Ca^{2+}$ Channel Blockers: Implications for $Na^+$and N–type $Ca^{2+}$ Channels Blockades," *Calcium Ion Modulators, Sel Pap Satell Symp* (1988) 13–23.

Vadodaria et al., "Synthesis and Central Nervous System Depressant Activity of New Piperazine Derivatives and Related Compounds. II," *J Med Chem* (1969) 12:860–865.

Zikolova et al., "Analogs of 1N–benzhydryl–4N–cinnamylpiperazine (cinnarizine). V. New N1–benzhydryl–N4–substituted Piperazines," *Tr Nauchnoizsled Khim—Farm Inst* (1984) 14:23–28 (Database Chemabs 'Online! Chemical Abstracts Service, Columbus, Ohio, AN: 103:37454, XP002133053).

Zikolova et al., "Analogs of N1–benzhydryl–N4–cinnamylpiperazine (cinnarizine). II. N1–substituted–N4–benzhydrylpiperazines," *Tr Nauchnoizsled Khim—Farm Inst* (1972) 8:59–67 (Database Chemabs 'Online! Chemical Abstracts Service, Columbus, Ohio, AN: 78:147908, XP002133054).

Bourinet et al., "Splicing of $\alpha_{1A}$ Subunit Gene Generates Phenotypic Variants of P–and Q–Type Calcium Channels," *Nature Neuroscience* (1999) 2:407–415.

Cribbs et al., "Cloning and Characterization of α1H from Human Heart, A Member of the T–Type $Ca^{2+}$Channel Gene Family," *Circulation Research* (1998) 83:103–109.

De Waard et al., "Structural and Functional Diversity of Voltage–Activated Calcium Channels," *ION Channels* (Narahashi, T. ed. Plenum Press, NY 1997) 4:41–87.

Dooley, "Lomerizine Kanebo KK" Current Opinion in CPNS Investigational Drugs (1999) 1(1):116–125.

Dunlap et al., "Exocytotic $Ca^{2+}$Channels in Mammalian Central Neurons," *Trends Neurosci* (1995) 18:89–98.

Galizzi et al., "Neuroleptics of the Diphenylbutylpiperidine Series are Potent Calcium Channel Inhibitors," *Proc Natl Acad Sci USA* (1986) 83:7513–7517.

Gould et al., "Antischizophrenic Drugs of the Diphenylbutylpiperidine Type Act as Calcium Channel Antagonists," *Proc Natl Acad Sci* (1983) 80:5122–5125.

Grantham et al., "Fluspirilene Block of N–Type Calcium Current in NGF–Differentiated PC12 Cells,"*Brit J Pharmacol* (1994) 111:438–488.

Ito et al., "U–92032, a T–Type $Ca^{2+}$Channel Blocker and Antioxidant, Reduces Neuronal Ischemic Injuries," *Eur J Pharmacol* (1994) 257:203–210.

King et al., "Substituted Diphenylbutylpiperidines Bind to a Unique High Affinity Site on the L–Type Calcium Channel," *J Biol Chem* (1989) 264:5633–5641.

Lee et al., "Cloning and Expression of a Novel Member of the Low Voltage–Activated T–Type Calcium Channel Family," *Journal of Neuroscience* (1999) 19:1912–1921.

McCleskey et al., "Functional Properties of Voltage Dependent Calcium Channels," *Curr Topics Membr* (1991) 39:295–326.

Perez–Reyes et al., "Molecular Characterization of a Neuronal Low–Voltage–Activated T–Type Calcium Channel," *Nature* (1998) 391:896–900.

Sather et al., "Distinctive Biophysical and Pharmacological Properties of Class A (BI) Calcium Channel $\alpha_1$ Subunits," *Neuron* (1993) 11:291–303.

Stea et al., "Localization and Functional Properties of a Rat Brain $\alpha_{1A}$ Calcium Channel Reflect Similarities to Neuronal Q–and P–Type Channels," *Proc Natl Acad Sci USA* (1994) 91:10576–10580.

Stea et al., Handbook of Receptors and Channels (North, R.A. ed. CRC Press 1995) 113–151.

\* cited by examiner

Penfluridol:

Pimozide:

Haloperidol:

Flunarizine:

FIG. 1

Tolylpiperazine—HCl

Procaine

Piperine

Trifluoromethylphenothiazine

Fomocaine

Morpholineacetophenone

Flocainide

Morpholinebenzophenone

FIG. 2A

Prenylamine
$\alpha_{1B}$ N-type: IC50>40uM

Pridimol
$\alpha_{1B}$ N-type: IC$_{90}$>400uM

Primidone
$\alpha_{1B}$ N-type: IC$_{50}$>500uM

Piperidolate
$\alpha_{1B}$ N-type: IC$_{50}$>300 uM

FIG. 2B

CALCIUM CHANNEL BLOCKERS

This application is a continuation-in-part of U.S. Ser. No. 09/107,037 filed Jun. 30, 1998 and now U.S. Pat. No. 6,011,035, and the contents of which are incorporated herein by reference.

TECHNICAL FIELD

The invention relates to compounds useful in treating conditions associated with calcium channel function. More specifically, the invention concerns compounds containing benzhydril and 6-membered heterocyclic moieties that are usefull in treatment of conditions such as stroke and pain.

BACKGROUND ART

Native calcium channels have been classified by their electrophysiological and pharmacological properties as T, L, N, P and Q types (for views see McCleskey, E. W. et al. *Curr Topics Membr* (1991) 39:295–326, and Dunlap, K. et al. *Trends Neurosci* (1995) 18:89–98). T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are usefull to further distinguish them. L-type channels are sensitive to dihydropyridine agonists and antagonists, N-type channels are blocked by the *Conus geographus* peptide toxin, ω-conotoxin GVIA, and P-type channels are blocked by the peptide aagatoxm IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A et al. *Neuron* (1995) 11:291–303; Stea, A. et al. *Proc Natl Acad Sci USA* (1994) 91:10576–10580; Bourinet, E. etal. *Nature Neuroscience* (1999) 2:407415). Several types of calcium conductances do not fall neatly into any of the above categories and there is variability of properties even within a category suggesting that additional calcium channels subtypes remain to be classified.

Biochemical analyses show that neuronal high voltage activated calcium channels are hetero oligomeric complexes consisting of three distinct subunits ($\alpha_1$, $\alpha_2\delta$ and $\beta$) (reviewed by De Waard, M. et at. *Ion Channels* (1997) vol. 4, Narahashi, T. ed. Plenum Press, NY). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of $\gamma$-subunit-encoding cDNAs is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$–$\alpha_{1I}$ and $\alpha_{1S}$ and correlated with the subtypes set forth above. $\alpha_{1A}$ channel s are of the P/Q type; $\alpha_{1B}$ represents N; $\alpha_{1C}$, $\alpha'_{1D}$, $\alpha_{1F}$ and acs represent L; $\alpha_{1E}$ represents a novel type of calcium conductance, and $\alpha_{1G-\alpha1I}$ represent members of the T-type family, reviewed in Stea, A. et al. in Handbook of Receptors and Channels (1994), North, R. A. ed. CRC Press; Perez-Reyes, et al. *Nature* (1998) 391:896–900; Cribbs, L. L. et al. *Circulation Research* (1998) 83:103–109; Lee, J. H. et al. *Journal of Neuroscience* (1999) 19:1912–1921.

U.S. Pat. No. 5,646,149 describes calcium antagonists of the formula A—Y—B wherein B contains a pipelazine or piperidine ring directly linked to Y. An essential component of these molecules is represented by A, which must be an antioxidant; the pipeazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin dervatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to mantain functionality.

Certain compounds containing both benzhydril moieties and piperidine or piperazine are known to be calcium channel antagonists and neuroleptic drugs. For example, Gould, R. J. et al. *Proc Natl Acad Sci USA* (1983) 80:5122–5125 describes antischizophrenic neuroleptic drugs such as lidoflaine, fluspirilene, pimozide, clopimozide, and penfluridol. It has also been that fluspirilene binds to sites on L-type calcium channels (King, V. K. et al. *J Biol Chem* (1989) 264:5633–5641) as well as blockdng N-type calcium cuerent (Grantm C. J. etal. *Brit J Pharmacol* (1944) 111:483–488). In addition, lomerizine, as marketed by Kenebo K K, is a known calcium channel blocker. A review of publications concerning lomeriine is found in Dooley, D., Current *Opinion in CPNS Investigational Drugs* (1999) 1:116–125.

The present invention is based on the recognition that the combination of a six-membered heterocyclic ring contaiing at least one nitrogen coupled optionally through a linker to a benzhydril moiety not only results in calcium channel blocking activity, but also enhanced specificity for N-type channels, thus making these compounds particularly useful for treating stroke and pain. By focusing on these moieties, compounds useful in treating indications associated with excessive calcium channel activity and combinatorial libraries that contain these compounds can be prepared.

DISCLOSURE OF THE INVENTION

The invention relates to compounds usefull in treating conditions such as stroke, chronic and acute pain, epilepsy, hypertension, cardiac arrhytmias, and other indications associated with calcium metabolism. The compounds of the invention are benzhydril derivatives of piperidine, piperazine, or morpholine with substituents which enhance the calcium channel blocking activity of the compounds but do not contain substituents that are antioxidants, tropholones or coumarins. Thus, in one aspect, the invention is directed to therapeutic methods that employ compounds of the formula (1)

wherein m is 0, 1 or 2;

wherein when m is 0, Z is O, when m is 1, Z is N, and when m is 2, Z is C;

Y is H, OH, $NH_2$, or an organic moiety of 1–20C, optionally additionally containing 1–8 heteroatoms selected from the group consisting of N, P, O, S and halo;

each $1^1$ and $1^2$ is independently 0-5;

$1^3$ is 0 or 1;

each of $R^1$, $R^2$ and $R^3$ is independently alkyl (1–6C), aryl (6–10C) or arylalkyl (7–16C) optionally containing 14 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1–4C) or alkyl (1–6C);

n is 0 or 1;

X is a linker, with the proviso that Y is not a tropolone, a coumarin, or an antioxidant containing an aromatic group and with the fuirther proviso that if $1^3$ is 0, neither $R^1$ nor $R^2$ represents F in the para position.

The invention is direct to methods to antagonize calcium channel activity using the compounds of formula (1) and thus to treat associated conditions. It will be noted that the conditions may be associated with abnormal calcium channel activity, or the subject may have normal calcium channel function which nevertheless results in an undesirable physical or metabolic state. In another aspect, the invention is directed to pharmaceutical compositions containing these compounds.

The invention is also directed to combinntorial libraries containing the compounds of formula (1) and to methods to screen these libraries for members containing particularly potent calcium channel blocking activity or for members that antagonize oter receptors. The libraries may also contain compounds of formula (1) where the provisos do not apply.

MODES OF CARRYING OUT THE INVENTION

The compounds of formula (1), useful in the methods of the invention, exert their desirable effects through their ability to antagonize the activity of calcium channels. While the compounds of formula (1) generally have this activity, the availability of a multiplicity of calcium channel blockers permits a nuanced selection of compounds for particular disorders. Thus, the availability of this class of compounds provides not only a genus of general utility in indications that are affected by excessive calcium channel activity, but also provides a large number of compounds which can be mined and manipulated for specific interaction with particular forms of calcium channels. The availability of recombinantly produced calcium channels of the $\alpha_{1A}$–$\alpha_{1I}$ and $\alpha_{1S}$ types set forth above, facilitates this selection process. Dubel, S. J. et al. *Proc Natl Acad Sci USA* (1992) 89:5058–5062; Fujita, Y. et al. *Neuron* (1993) 10:585–598; Mikami, A. et al. *Nature* (1989) 340:230–233; Mori, Y. et al. *Nature* (1991) 350:398402; Snutch, T. P. et al. *Neuron* (1991) 7:45–57; Soong, T. W. et al. *Science* (1993) 260:1133–1136; Tomlinson, W. J. et al. *Neuropharmacology* (1993) 32:1117–1126; Williams, M. E. et al. *Neuron* (1992) 8:71–84; Williams, M. E. et al. *Science* (1992) 257:389–395; Perez-Reyes, et al. *Nature* (1998) 391:896–900; Cribbs, L. L. et al. Circulation Research (1998) 83:103–109; Lee, J. H. et al. *Journal of Neuroscience* (1999) 19:1912–1921.

Thus, while it is known that calcium channel activity is involved in a multiplicity of disorders, the types of channels associated with particular conditions is the subject of ongoing data collection. The association of, for example, N-type channels, as opposed to other types, in a specific condition would indicate that compounds of the invention which specifically target N-type receptors are most useful in this condition. Many of the members of the genus of compounds of formula (1) are likely to specifically target N-type channels. Other members of the genus may target other channels Among the conditions associated in which blocking excessive calcium would be of therapeutic value are stroke, epilepsy, and chronic and acute pain. Other cardiovascular conditions include hypertension and cardiac arrhythnnas. Calcium is also implicated in other neurological disorders such as migraine, epilepsy and certain degenerative disorders.

The availability of the libraries containing the compounds of formula (1) (including those to which the provisos do not apply) also provides a source of compounds which may be screened for activity with regard to additional ion channels and receptors. These channels and receptors are also associated with conditions that are susceptible to treatment. Blockers of sodium channels, for example, are usefull as local anesthetics, and in treating cardiac arrhythmias, as anticonvulsants, and in treating hyperdemic periodic paralysis. Potassium channel blockers are useful in treating hypertension and cardiac affhythnmias; various other receptors are associated with psychoses, schizophrenia, depression, and apnea Thus, the library of compounds of the invention is useful in standard screening techniques as a source of effective pharmaceutical compounds.

The compounds of the invention may be synthesized using conventional methods. Illustrative of such methods are Schemes 1 and 2:

Scheme 1 (Z is N)

-continued

↓ H₂/Pd

↓ BH₃

Alternatively, a carboxylic acid containing the benzhydril moiety can be synthesized and then reacted with the piperazine (or piperidine) moiety and subsequently reduced. Under those circumstances, an ω-bromo carboxylic acid is refluxed with triphenylphosphine in the presence of methyl nitrile and then treated with lithium hexamethyldisilazide in a solvent such as THF. The resulting unsaturated carboxylic acid containing the two phenyl substituents is then reduced as shown in Scheme 1 with hydrogen on a palladium catalyst and then reacted with derivatized piperazine (or pipendine) to form the amide. The amide can then be reduced as shown above.

Scheme 2 (Z is CH)

The compounds of formula (1) are defined as shown in terms of the embodiments of their various substituents:

Z may be O, N or C where m has the appropriate value, i.e., O when m is 0, N when m is 1 or C when m is 2.

When m is 2, one of the Y substituents is preferably H, OR, $NR_2$, wherein R is H alkyl (1–6C) or one Y may be itselfalkyl (1–6C). Preferred forms of Z are N, and C where one Y is H or OH.

Y is H, OH or $NH_2$, or an organic moiety of 1–25C, optionally additionally containing 1–8 heteroatoms selected from the group consisting of N, P, O, S and halo. Preferred forms of at least one Y include those that comprise an aromatic ring system, including fised ring systems and rings containing one or more heteroatoms. Particularly preferred forms of at least one Y are those which include phenyl moieties. The aromatic moieties included within Y may be substituted or unsubstituted; the "substituents" may include alkyl (1–6C), halo, OR, SR, $NR_2$, COOR, or $CONR_2$ wherein each R is independently H or alyl (1–6C) or the "substituents" may be CN, $CF_3$, or $NO_2$. This set of moieties will be referred to herein as "substituents." Of course, if Z is O, Y is not present (m=0).

Additional preferred embodiments of Y include: aminoindane, azulene, cyclohexane, cyclohexanol, hexahydroazepin, indane, indene, indazole, indole, indolazine, morpholine, phenothiazine, phenoxazine, piperidine, pyrrole, pyridine, pyrimidine, thionaphthene, thiomorpholine, thiazine, and thiazole or these systems linked through an additional linker. When m is 2, the two Y groups may be the same or different and preferred forms are those set forth above. Particularly preferred, however, are embodiments where, when m is 2 and Z is C, one Y is selected from the foregoing list and the other Y is H or OH.

$R^3$ may be alkyl (1–6C) aryl (6–10C), or arylalkyl (7–16C) optionally containing 1–4 heteroatoms selected from the group consisting of N, P, O, S, and halo; preferred embodiments of $R^3$ include methyl. Typically, $1^3$ is 0 or 1.

As n may be 0 or 1, X may be present or not X is a suitable linker containing 1–10C which may be saturated or unsaturated and may contain a ring. The linker may also contain one or two heteroatoms selected from N, O and S and may be substituted with the "substituents" listed above. Preferred embodiments of X include —$(CH_2)_n$— wherein n is 1–10, preferably 1–6.

$R^1$ and $R^2$ may independently be alkyl (1–6C) aryl (6–1OC), or arylalkyl (7–16C) optionally containing 1–4 heteroatoms and optionally containing any of the "substituents" set forth above or $R^1$ and $R^2$ may themselves independently be said substituents; $1^1$ and $1^2$ are each independently 0–5, but preferably 0–3. Preferred embodiments of $1^1$ and $1^2$ include 1, where the substiuent is in the pam position (1p) or 3 where the substituents are in the two ortho positions and the psra position (3o,p) or 2 where the substituents are in the meta positions (2m). Prefered forms of $R^1$ and $R^2$ include phenyl, phenylalkli, Cl, Br, I, $CF_3$, amino and alkl.

In the methods of treatment using the compounds of formula (1), Y must be other than a tropolone, a coumarin, or an oxidant containing an aromatic group. In addition, in these methods the compounds of formula (1) cannot include those wherein $1^3$ is 0 and either $R^1$ or $R^2$ resents F in the para position In the libraries containing compounds of formula (1), these provisos do not apply.

Preferred compounds for use in the method of the invention include those of the formulas (1a)

(1a)

wherein Z is N or CH;
wherein each of $n^1$ and $n^2$ is independently 0 or 1;
$X^1$ and $X^2$ are linkers; and
Ar represents one or two substituted or unsubstituted aromatic or heromatic rings, and of (1b)

(1b)

wherein Z is N or CH;
wherein each of $n^1$ and $n^2$ is independently 0 or 1;
$X^1$ and $X^2$ are linkers; and
Cy reesents one or two substituted or unsubstituted aliphatic cyclic or heterocyclic moieties, or consists of one substituted or unsubstituted aliphatic cyclic or heterocyclic moiety and one substituted or unsubstituted aromatic or heteroaromatic moiety.

Thus, fonnulas (1a) and (1b) are similar, except that compounds of formula (1a) contain aromatic substituents linked to the hetrocyclic 6-membered ring and those of (1b) contain aliphatic cyclic or heterocyclic moieties. In each case, preferably when $X^2$ is present, $X^2$ represents a linker which spaces the Ar or Cy moiety from Z at a distance of 3–20 Å, and may contain at least one heteroatom which is nitrogen or oxygen. Included in such linkers are amines and carbonyl functionalities, including amides. The linker may also be unsaturated or may be an alkylene group. Typically, $X_2$ is $(CH_2)_{1-8}$ or $(CH_2)_{1-5}-CH=CH-(CH_2)_{0-3}-$. Similarly, $X^1$, when present, spaces the benzhydril moiety from the nitrogen of the heterocyclic ring at a distance of 3–20 Å and may contain a heteroatom. Prefelred embodiments are similar to those for $X^2$.

In both cases, when there are two aromatic or heterocyclic moieties, $X^2$ must accommodate this and a typical embodiment is $-(CH_2)_{0-6}-CH$, which may also contain a π-bond.

Thus, in preferred forms of formulas (1a) and (1b), $n^1$ is 1 and $X^1$ is $(CH_2)_{1-5}CO(CH_2)_{0-3}$, $(CH_2)_{1-5}NH(CH_2)_{0-3}$, $(CH_2)_{1-5}CONH(CH_2)_{0-3}$, and $(CH_2)_{1-5}NHCO(CH_2)_{0-3}$.

The prefered embodiments for $X^2$ are similar except that in instances where Ar or Cy represent two nngs, the two rings are coupled to CH as the terminal portion of the linker $X^2$. When $X^1$ and $X^2$ are selected from these preferred embodiments, although it is preferred that $1^1$ and $1^2$ are both 0, substitution by $R^1$ and $R^2$ in the benzhydril system is permitted as set forth in the description of the invention above, and may also include, in these instances, a para-fluoro substituent.

It is believed that halogenation of the compounds of the invention is helpfiul in modulating the in vivo half-life, and it may be advantageous to include halogen substituents as $R^1$ and $R^2$. In formulas (1a) and (1b), such substituents may also be included on Ar and Cy.

The invention compounds may also be supplied as pharmaceutically acceptable salts. Pharmaceutically acceptable salts include the acid addition salts which can be formed from inorganic acids such as hydrochloric, suliric, and phosphoric acid or from organic acids such as acetic, propionic, glutamic, glutaic, as well as acid ion-exchange resins.

UTILITY AND ADMINISTRATION

For use as treatment of animal subjects, the compounds of the invention can be formulated as pharmaceutical or veterinary compositions. Dcepnding on the subject to be treated, the mode of adminision, and the type of ant desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa.

In general, for use in treatment, the compounds of formula (1) may be used alone, as mixtures of two or more compounds of formula (1) or in combination with other pharmaceuticals. Depending on the mode of administration, the compounds will be formulated into suitable compositions to permit facile delivery.

Formulations may be prepared in a manner suitable for systemic administration or topical or local admiation. Systemic formulations include those designed for injection (e.g., intramuscula, intravenous or subcutaneous injection) or may be prepared for transdermal, transmucosal, or oral administration The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the ike. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as ithe use of suppositories, transdermal patches, trarsmucosal delivery and intranasal administration. Oral administration is also suitable for compounds of the invention. Suitable forms include s capsules, tablets, as in understood in the art.

For administrrtion to animal or human subject, the dosage of the compounds of the invention is typically 0.1–100 μg/kg. However, dosage levels are highly dependent on the nature of the condition, the condition of the patient, the judgment of the practitioner, and the frequency and mode of admniistration.

Screening Methods

The compounds of the invention can be synthesized individually using methods known in the art per se, or as members of a combinatorial library. In general, the benzhydril portion of the molecule, typically containing any $R^1$ and $R^2$ substituents is coupled, along with any lining moiety, to the nitrogen of the morpholine, piperazine or piperidine ring. This ring itself is generally appropriately substituted prior to this coupling. Typically, the benzhydril-linker portion is supplied containing a suitable electron-withdrawing leaving group, thus effecting the coupling to the ring nitrogen.

In addition to condensing a halogenated derivative of a benzhydril moiety to the nitrogen-containing heterocycle, additional conventional ways of condensing the relevant portions of the molecule can be used. For example, a brominated form of appropriately substituted benzhydril may be converted to a Grignard reagent which can then be condensed with, for example, the morpholine, piperidine, or piperazine ring extended at the nitrogen through the moiety $(CH_2)_n CHO$ wherein n is an integer from 1–4. Alternatively, a bromoaqlylated form of the nitrogen-containing heterocycle may be converted to a Grignard reagent and condensed with the appropriately substituted diphenylketone. In addition, an aminoalkylated forn of the nitrogen-containing heterocycle may be condensed with appropriately substituted diphenylketone to obtain the imine which can then be reduced, if desired. Finally, the two phenyl moieties associated with the benzhydril group can be prepared separately and condensed to obtain benzhydril alcohol using a Grignard reagent prepared from one phenyl group and the appropriately substituted benzaldehyde. The benzhydril alcohol can then be brominated or further extended by alkylation and condensed with the morpholine, piperidine or piperazine derivative.

Synthesis of combinatorial libraries is now commonplace in the art. Suitable descriptions of such syntheses are found, for example, in Wentworth, Jr., P. et al. Current *Opinion in Biol* (1993) 9:109–115; Salemme, F. R. et al. *Structure* (1997) 5:319–324. The libraries contain compounds with various embodiments of $R^1$, $R^2$, $R^3$, X, Y and Z. These libraries, which contain, as few as 10, but typically several hundred members to several thousand members, may then be screened for compounds which are particularly effective against a specific subtype of calcium channel. In addition, using standard screening protocols, the libraries may be screened for compounds which block additional channels or receptors such as sodium channels, potassium channels and the like.

Methods of performing these screening functions are well known in the art. Typically, the receptor to be targeted is expressed at the surface of a recombinant host cell such as human embryonic kidney cells. The ability of the members of the library to bind the receptor or channel is measured, for example, by the ability of the compound in the library to displace a labeled binding ligand such as the ligand normally associated with the receptor or an antibody to the receptor. More typically, ability to antagonize the receptor is measured in the presence of the appropriate agonist and the ability of the compound to interfere with the signal generated is measured using standard techniques.

In more detail, one method involves the binding of radiolabeled agents that interact with the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the calcium channel are recorded before and after application of the compound of interesl Another method, high-throughput spectrophotometric assay, utilies loading of the cell lines with a fluorescent dye sensitive to intracellular calcium concentration and subsequent examination of the effects of compounds on the ability of depolarzation by potassium chloride or other means to alter intracellular calcium levels.

The following examples are intended to illustrate but not to limit the invention.

EXAMPLE 1

Correlation of Calcium Channel Block with the Presence of a Piperidine/Piperazine Ring Antagonist activity was measured using nystatin patch recordings on human embryonic kidney cells either stably or transiendy expressing rat $\alpha_{1B+\alpha 2b}+\beta_{1b}$ channels with 5 mM barium as a charge carrier.

For transient expression, host cells, such as human embryonic kidney cells, HEK 293 (ATCC# CRL 1573) are grown in standard DMEM medium supplemented with 2 mM gluiaine and 10% fetal bovine serer. HEK 293 cells are transfected by a standard calcium-phosphate-DNA coprecipitation method using the rat $\alpha_{1B}+\beta_{1b}+\alpha_2\delta$ N-type calcium channel subunits in a vertebrate expression vector (for example, see *Current Protocols in Molecular Bioloy*).

After an incubation period of from 24 to 72 hrs the culture medium is removed and replaced with external recording solution (see below). Whole cell patch clamp experiments are performed using an Axopatch 200B amplifier (Axon Instrrnents, Burlingame, Calif.) linked to an IBM compatible personal computer equipped with pCLAMP software. The external recording solution is 5–20 mM $BaCl_2$, 1 mM $MgCl_2$, 10 mM HEPES, 40 mM TEACl, 10 mM Glucose, 65 mM CsCl (pH 7.2). The internal pipette solution is 105 mM CsCl, 25 mM TEACl, 1 mM $CaCl_2$, 11 mM EGTA, 10 mM HEPES (pH 7.2). Currents are typically elicited from a holding potential of −100 mV to various test potentials. Data are filtered at 1 kHz and recorded directly on the hard drive of a personal computer. Leak subtraction is carried out on-line using a standard P/5 protocol. Currents are analyzed using pCLAMP versions 5.5 and 6.0. Macroscopic current-voltage relations are fitted with the equation $I=\{1/(1+\exp(-(V_m-V_h)/S)\} \times G-(V_m-E_{rev})$, where $V_m$ is the test potential, $V_h$ is the voltage at which half of the channels are activated, and S reflects the steepness of the activation curve and is an indication of the effective gating charge movement Inactivation curves are normalized to 1 and fitted with $I=(1/1+\exp((V_m-V_h)/S)$ with $V_m$ being the holding potential.

Figure 1:
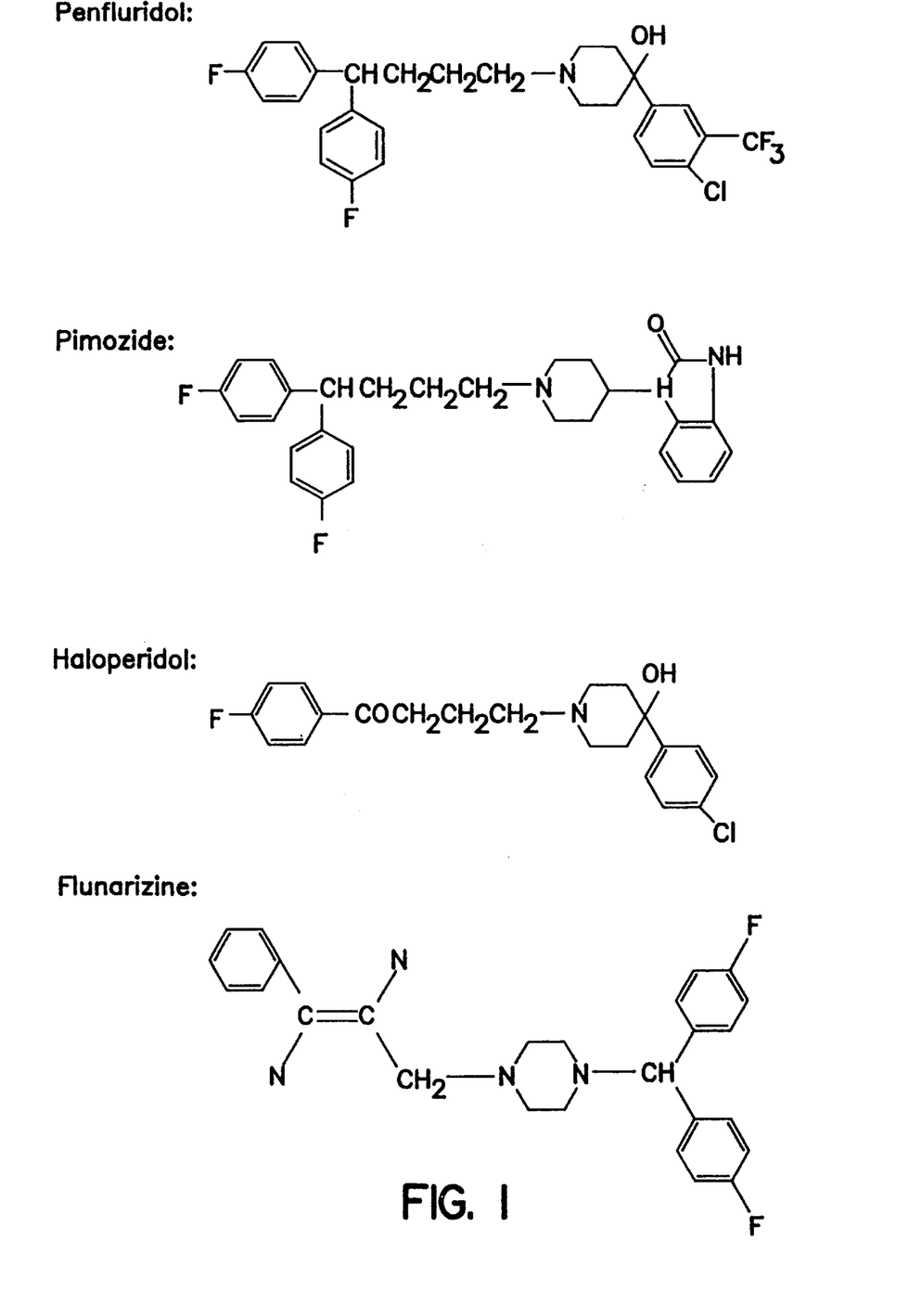
FIG. 1 shows the structure of several known compounds which have been shown to exhibit calcium channel antagonistic activity.
Figure 2A:
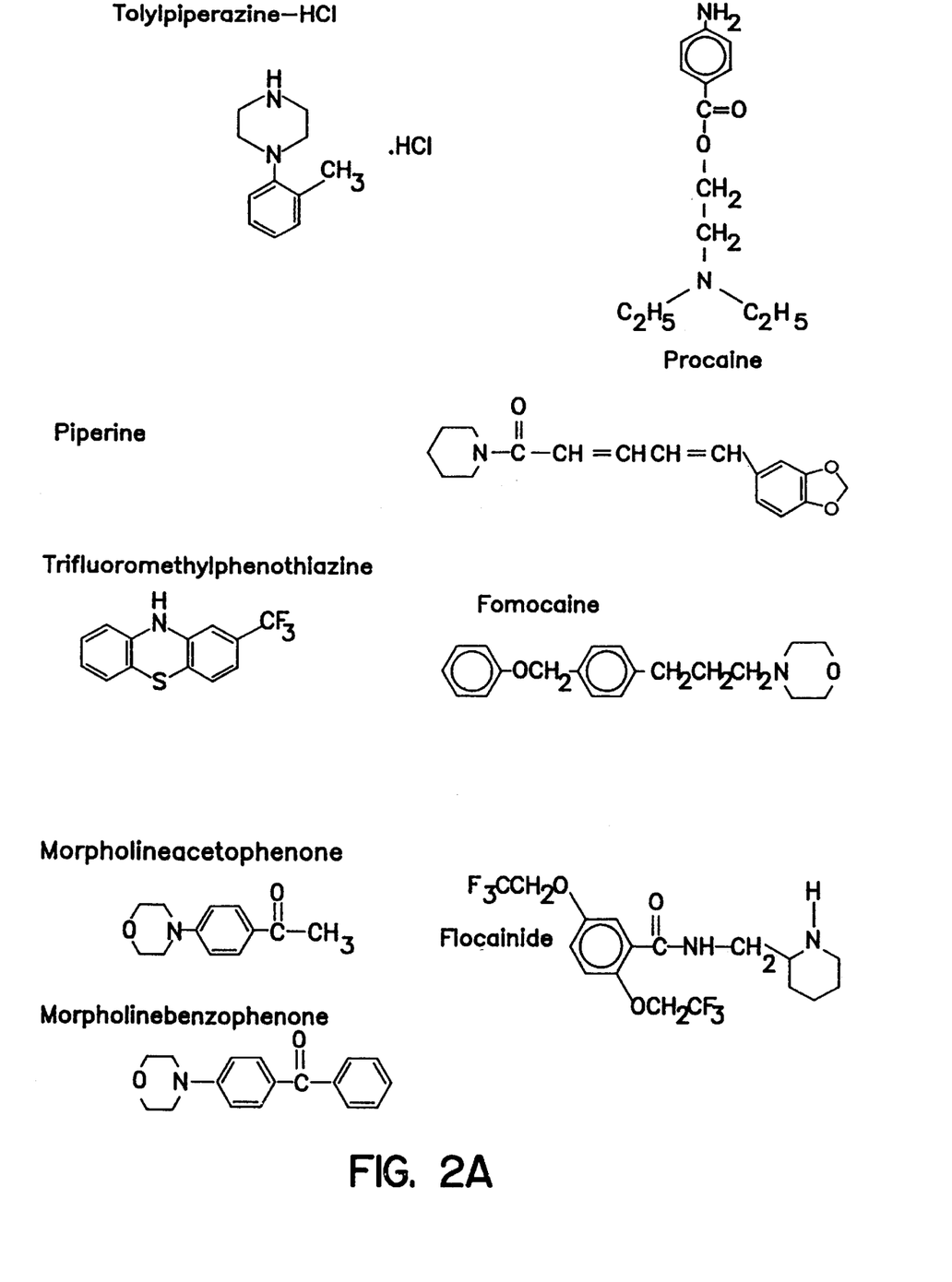
FIG. 2 shows the structure of several known compounds which have been demonstrated to lack calcium channel blocking activity at acceptable concentaions.
Figure 2B:
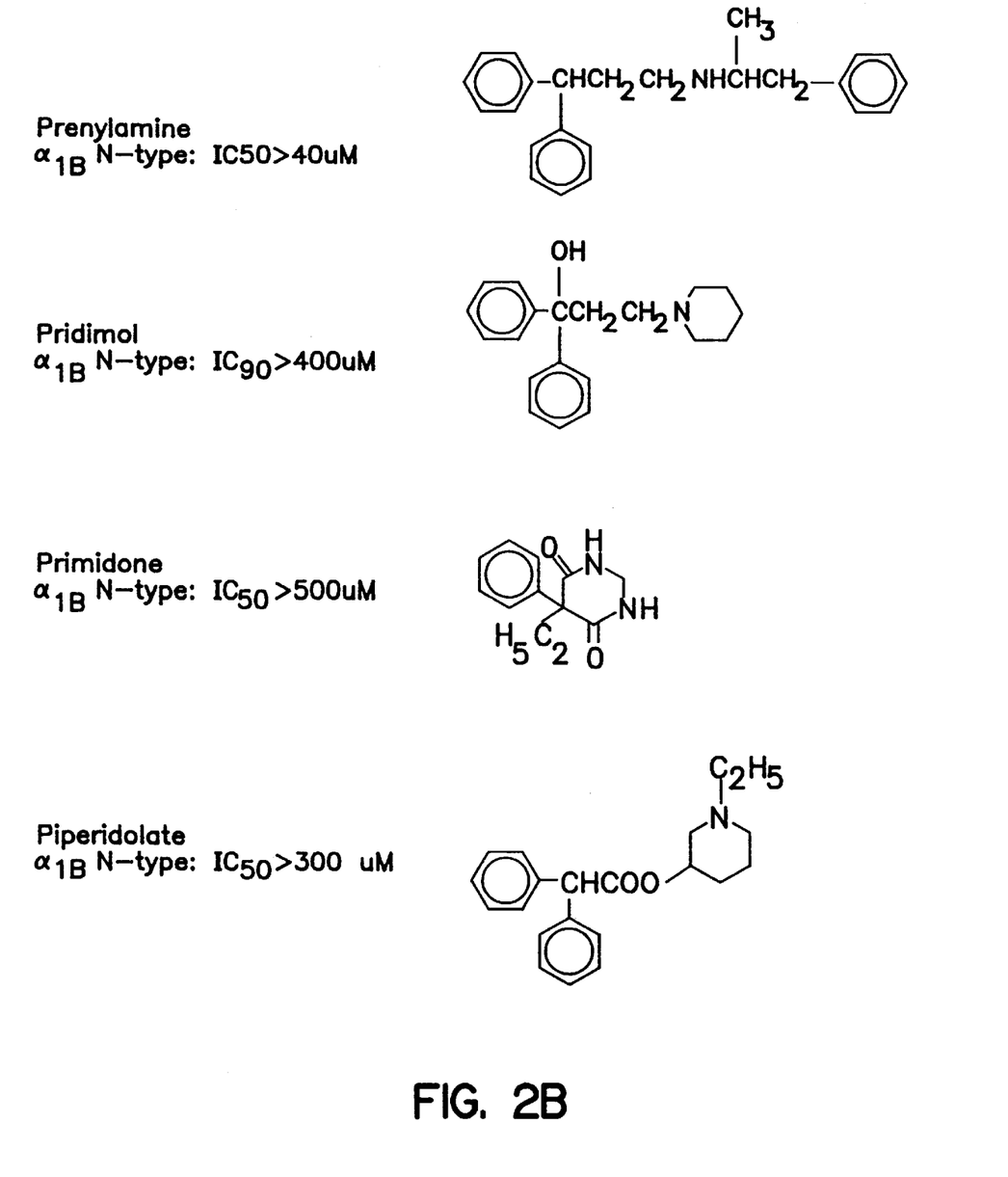

The results of three extents were averaged. The structures of most of the compounds tested are shown in FIGS. 1 and 2. The compounds of FIG. 1 showed effective blocking activity:

Penfluridol has an $IC_{50}$ of 5 $\mu M$; the block develops over 60–90 sec at 10 $\mu M$ concentrations and is poorly reversible (pKa=9.0).

Pimozide shows an $IC_{50}$ of about 2–3 $\mu M$; the block develops in 90 sec at 10 $\mu M$ and is completely reversible (pKa=7.32). More than 80% of the activity is blocked at 10 $\mu M$.

Haloperidol has an $IC_{50}$ of 90 $\mu M$ and the block develops in less than 16 sec. It is reversible within 15 sec (pKa8.3). At 10 $\mu M$ concentrations, the block is about 10%.

Flunarizine has an $IC_{50}$ of <1 $\mu M$; the block develops over about 120 sec at 10 $\mu M$ concentration and reveres over about 5 min. The block is 90–95% effective at 10 $\mu M$.

On the other hand, less activity was shown by prenylamine ($IC_{50}$>40 $\mu M$); pridinol ($IC_{50}$>400 $\mu M$); primidone ($IC_{50}$>500 μM); and piperidolate ($IC_{50}$>300 μM). Additional compounds which showed high values for $IC_{50}$ include bupivacaine, tolylpiperazine, piperine, trifluoromethylphenothiazine, morpholineacetophenone, morpholinebenzophenone and chloroethylpiperaine. As shown, the compounds of formula (1) which show activity comprise those wherein the CH atached to X is in turn bound to two phenyl rings and Y contains one phenyl ring, optionally substituted by halo.

EXAMPLE 2

Synthesis of Illustrative Compounds of Formula (1)
A. Synthesis of 6,6-Diphenyl Hexanoic Acid.

6-Bromohexanoic acid (7.08 g, 36.3 mmole) and triphenylphosphine (10 g, 38.2 mmole) were niixed in dry $CH_3CN$ (40 ml), heated to reflux overnight and allowed to cool to RT. The solution was concentrated under reduced pressure to give a viscous gel. Approximately 75 ml of THF was added to the reaction mixture and the walls of the flask were scratched with a spatula to start crystallizon. The resulting solid was filtered under vacuum, washed with THF and dried under reduced pressure and used without further purification.

This product (1.5 g) was suspended in dry THF (10 ml) and the flask purged with $N_2$ and cooled to –78° C. To the stirred reaction was added lithium hexamethyldisilazide (LiHMDS) (10 ml, 1M in THF). The yellow solution was sired at –78° C. for 1 h over which time the reaction darkened slightly. The cooling bath was removed and the reaction allowed to warm to RT. The reacion was kept at RT for 1h during which time the solution turned a dark red color and most of the solids went into solution. Benzophenone (0.54 g in 3 ml THF) was added to the reacon and allowed to react overnight. The yellow solution was concentrated under reduced pressure to give a yellow solid. The resulting solid was partitioned between ether and 10% HCl. The organic layer was washed with water (2x) and extracted with 10% NaOH (3x). The combined aqueous base fraction was acidified with conc. HCl to a pH of 4. The water layer was extracted with ether (3x) and the combined organic fiadons dried over $Na_2SO_4$.

The ether was evaporated to dryness under reduced pressure to give a colorless oil which crystallied on standing to give a waxy solid, 6,6-diphenyl hex-5enoic acid, which was dissolved in 30 ml MeOH and mixed with 5% Pd-C and placed in a Parr hydrogenator. The reaction vessel was purged with hydrogen and prized to 60 PSIG and reacted at RT for 4 h. The reaction mixture was sampled and analyzed by TLC. If the TLC when stained with KMnO4 showed a positive test for alkenes the reaction mixture was resubjected to the reaction conditions. The solution was then filtered through a plug of celite and the methanol filtrate containig 6,6diphenyl hexanoic acid was concentrated under vacuum.

B. Reaction with Substituted Pipeperazine.

6,6-Diphenylhexanoic acid (0.4 mmoles) was mixed with the desired N-alkylated piperazine (0.35 mmoles) in dry THF (7ml). EDC (0.5 mimoles) and DMAP (cat) were added and the mixur heated to 40° C with shaking overnight. The reaction was diluted with ethyl acetate and washed with water (4x) and 10% NaOH (3x) and dried over sodium sulfate and evaporated to dryness. The resulting residue was purified by column chromatography (silica gel, 1:1 hexane:EtOAc), and the products were characterized by HPLC-MS.

Piperazines used in the foregoing procedure include phenylpiperazine, benzylpiperazine, benzhydrilpiperazine, and piperazine substituted at the 1-position with BOC or φ—CH=$CH_2$—.

The resulting compounds contain a carbonyl adjacent to the ring nitrogen of piperazine. These compounds are of fonnula (1) and exhibit calcium ion channel blocking activity.

C. Reduction of CO in $X^1$.

The compounds prepared in paragraph B were dissolved in dry THF (5 ml) and * reacted with $LiAlH_4$ (M in THF) and allowed to react for 6 h. The reactions were quenched with EtOAc (15 ml) and extracted with water (5x) 10% NaOH (10x), brine (1x), dried over sodium sulfate and concentrated under reduced pressure. Most of the products at this stage were >80% pure. Those <80% were purified for running a short column (silica gel, 1:1 hex:EtOAc).

D. Preparation of Compounds of Formula (1) from Benzhydrylpiperazine Derivatives.

N-Diphenylmethyl)piperazine (0.5 mmole) was dissolved in dry THF (10 ml). To each reaction flask was added powdered $K_2CO_3$ and acid chloride of the formula Y'-CO-Cl (0.7 mmole). The reaction was stirred at RT for 2 h and quenched with 105 NaOH (10 ml) and extracted with EtOAc (10 ml). The organic layer was washed with 10% NaOH (4x) and dried over sodium sulfate, concentrated, and purified by column chromatography (silica gel, 1:1 hex:EtOAc) to give the desired amide. Acyl halides used in this procedure included cyclohexyl COCl, ΦCOCl and ΦCH=CHCOCl.

To reduce the resulting amide, the above product was dissolved in dry THF (5 ml) and reacted with LiAlH (1M in THF) and allowed to react for 6 h. The reaction was quenched with EtOAc (15 ml) and extracted with water (5x) 10% NaOH (10x), brine (1x), dried over sodium sulfate and concentrated under reduced pressure. Most of the products at this stage were >80% pure. Those <80% were purified for running a short column (silica gel, 1:1 hex:EtOAc).

EXAMPLE 3

Synthesis of Additional Compounds of Formula (1)

Following the general procedure described above in Reaction Schemes 1 and 2, the following compounds of fonnula (1) are synthesized as shown in Table A.

TABLE A

| $R^1$ | $L^1$ | $R^2$ | $I^2$ | X | n | Y | Y | $R^3$ | $I^3$ | Z | m |
|---|---|---|---|---|---|---|---|---|---|---|---|
| $CH_3$ | 1 p | $CH_3$ | 1 p | — | 0 | φ | — | — | 0 | N | 1 |
| — | 0 | Cl | 2 m | —$CH_2$— | 1 | —$CH_2$φ | H | $CH_3$ | 1 | CH | 2 |
| F | 1 p | F | 3 o, p | —$CH_2$—$CH_2$— | 1 | —$CH_2$CHφ | OH | $CH_3$ | 1 | COH | 2 |

TABLE A-continued

| R$^1$ | L$^1$ | R$^2$ | l$^2$ | X | n | Y | Y | R$^3$ | l$^3$ | Z | m |
|---|---|---|---|---|---|---|---|---|---|---|---|
| — | 0 | CF$_3$ | 1 p | — | 0 |  | H | C$_2$H$_5$ | 1 | CH | 2 |
| φ | 1 p | — | 0 | —(CH$_2$)$_3$— | 1 | Amino-indane | — | — | 0 | O | — |
| CH$_3$ | 3 o, p | COOMe | 2 m | —CH$_2$— | 1 | Azulene | Azulene | C$_2$H$_5$ | 1 | C | 2 |
| Cl | 3 o, p | Cl | 2 m | —CONH— | 1 | Cyclohexane | — | CH$_3$ | 1 | N | 1 |
| CN | 2 m | CF$_3$ | 2 m | —CH=CH— | 1 | Pyrimidine | — | — | 0 | N | 1 |
| N(CH$_3$)$_2$ | 1 p | C$_2$H$_5$ | 2 m | —CH$_2$CH$_2$— | 1 | Indole | Pyrrole | — | 0 | C | 2 |

EXAMPLE 4

Channel Blocking Activities of Various Invention Compounds

Using the procedure set forth in Example 1, various compounds of the invention were tested for their ability to block N-type calcium ion channels. The results are shown in Tables 1–3, where IC$_{50}$ is given in μM (micromolar). Table 1 represents results for compounds of formula (1a) where Z is CH; Table 2 represents results for compounds of formula (1a) where Z is N; and Table 3 represents the results the results for compounds of formula (1b) where Z is N. In all cases, $1^1$, $1^2$ and $1^3$ are 0.

TABLE 1

Formula (1a), Z is CH

| n$^1$ | X$^1$ | n$^2$ | X$^2$ | Ar | IC$_{50}$ | % reversibility |
|---|---|---|---|---|---|---|
| 1 | CH$_2$ | 1 | NHCH$_2$ | φ | 3 | 80 |
| 1 | (CH$_2$)$_2$ | 1 | NHCH$_2$ | φ | 2 | 67 |

TABLE 2

Formula (1a), Z is N

| n$^1$ | X$^1$ | n$^2$ | X$^2$ | Ar | IC$_{50}$ | % reversibility |
|---|---|---|---|---|---|---|
| 1 | (CH$_2$)$_6$ | 1 | CH$_2$ | φ | 2–5 | 52 |
| 1 | (CH$_2$)$_6$ | 1 | —CH$_2$—CH=CH— | φ | 1–3 | 44 |
| 1 | (CH$_2$)$_5$ | 0 | — | φ | ±10 | 83 |
| 1 | (CH$_2$)$_5$ | 1 | CH$_2$ | φ | ±5 | 71 |
| 1 | (CH$_2$)$_5$ | 1 | (CH$_2$)$_2$ | φ | 5–10 | 72 |
| 1 | (CH$_2$)$_4$CO | 1 | CH$_2$ | φ | ±5 | 66 |
| 1 | (CH$_2$)$_4$CO | 1 | —CH$_2$CH=CH— | φ | 2–3 | 58 |
| 1 | (CH$_2$)$_4$CO | 1 | —COCH$_2$— | φ | 5 | 78 |
| 1 | (CH$_2$)$_5$CO | 1 | CH$_2$ | φ | 2–5 | 84 |
| 1 | (CH$_2$)$_3$CO | 1 | —CH$_2$CH=CH— | φ | 2–5 | 39 |
| 1 | (CH$_2$)$_4$ | 0 | — | φ | 3–5 | 13 |
| 1 | (CH$_2$)$_4$ | 1 | —CH$_2$CH=CH— | φ | ±5 | 48 |
| 0 | — | 1 | (CH$_2$)$_2$CH | 2φ | 2–5 | 40 |
| 0 | — | 1 | COCH$_2$CH | 2φ | 2–5 | 40 |
| 1 | CH$_2$CO | 1 | COCH | 2φ | ±5 | 60 |
| 1 | CO | 1 | COCH | 2φ | >20 | 90 |
| 1 | CH$_2$CO | 1 | CH | 2φ | 2–5 | 40 |
| 1 | (CH$_2$)$_2$ | 1 | CH | 2φ | 2–5 | 40 |
| 1 | CO | 1 | CH | 2φ | >50 | — |
| 0 | — | 1 | CH$_2$ | φ | ±15 | 70 |
| 1 | CH$_2$ | 1 | CH$_2$ | φ | ±50 | 0 |
| 1 | CO | 1 | CH$_2$ | φ | ±50 | 85 |
| 1 | (CH$_2$)$_2$ | 1 | CH$_2$ | φ | ±20 | 70 |
| 1 | CO | 0 | — | φ | ±50 | 85 |
| 1 | CO | 1 | CH$_2$ | φ | ±50 | 85 |
| 1 | CO | 1 | CH | 2φ | >50 | — |
| 1 | CO | 1 | —CH$_2$CH=CH— | φ | ±50 | 90 |
| 1 | CH$_2$CO | 0 | — | φ | >50 | 90 |
| 1 | CH$_2$CO | 1 | CH$_2$ | φ | ±15 | 80 |
| 1 | CH$_2$CO | 1 | —CH$_2$CH=CH— | φ | ±20 | 80 |
| 1 | CH$_2$ | 0 | — | φ | >50 | 0 |
| 1 | CH$_2$ | 1 | CH$_2$ | φ | ±50 | 0 |
| 1 | CH$_2$ | 1 | CH | 2φ | >50 | 90 |
| 1 | CH$_2$ | 1 | CH$_2$CH=CH— | φ | 35 | 60 |
| 1 | (CH$_2$)$_2$CO | 0 | — | φ | ±9 | 11 |
| 1 | (CH$_2$)$_2$CO | 1 | CH$_2$ | φ | ±10 | 13 |
| 1 | (CH$_2$)$_2$CO | 1 | CH | 2φ | ±23 | 28 |
| 1 | (CH$_2$)$_2$CO | 1 | —CH$_2$CH=CH— | φ | ±5 | 20 |

TABLE 3

Formula (1b), Z is N

| n$^1$ | X$^1$ | n$^2$ | X$^2$ | Cy | IC$_{50}$ | % reversibility |
|---|---|---|---|---|---|---|
| 1 | CH$_2$ | 1 | NHCH | cyclohexyl | 3–4 | 62 |
| 1 | (CH$_2$)$_2$ | 1 | NHCH | cyclohexyl | 2–3 | 68 |
| 1 | (CH$_2$)$_6$ | 1 | CH$_2$ | cyclohexyl | ±1 | 5 |
| 1 | (CH$_2$)$_5$ | 1 | CH$_2$ | cyclohexyl | 5–10 | 66 |

What is claimed is:

1. A method to treat conditions associated with aberrant N-type calcium channel activity in a subject which method comprises administering to a subject in need of such treatment at least one compound of the formula (1)

wherein m is 0, 1 or 2;

wherein when m is 0, Z is O, when m is 1, Z is N, and when m is 2, Z is C;

Y is H, OH, NH$_2$, or an organic moiety of 1–20C, optionally additionally containing 1–8 heteroatoms selected from the group consisting of N, P, O, S and halo;

each $1^1$ and $1^2$ is independently 0–5;

$1^3$ is 0 or 1;

each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or each of $R^1$ and $R^2$ may independently be halo, COOR, CONR$_2$, CF$_3$, CN or NO$_2$, wherein R is H or lower alkyl (1–4C) or alkyl (1–6C);

n is 0 or 1;

X is a linker;

with the proviso that Y is not a tropolone, a coumarin, or an antioxidant containing an aromatic group and with the further proviso that if $1^3$ is 0, neither $R^1$ nor $R^2$ can be F in the para position said compound being administered in an amount effective to modulate N-type calcium channel activity.

2. The method of claim 1 wherein at least one of $R^1$, $R^2$ and $R^3$ is a halo substituent.

3. The method of claim 1 wherein the compound of formula (1) is of the formula (1a)

(1a)

wherein Z is N or CH;

wherein each of $n^1$ and $n^2$ is independently 0 or 1;

$X^1$ and $X^2$ are linkers; and

Ar represents one or two substituted or unsubstituted aromatic or heteroaromatic rings.

4. The method of claim 3 wherein Ar represents one or two unsubstituted phenyl moieties.

5. The method of claim 3 wherein $n^2$ is 1 and $X^2$ represents a linker which spaces Ar from Z at a distance of 3–20 Å.

6. The method of claim 5 wherein $n^2$ is 1 and $X^2$ contains at least one heteroatom selected from N and O.

7. The method of claim 5 wherein $n^2$ is 1 and $X^2$ represents —(CH$_2$)$_{1-8}$— or —(CH$_2$)$_{1-5}$—CH=CH—(CHCH$_2$)$_{0-3}$—.

8. The method of claim 5 wherein Ar represents two phenyl moieties and $n^2$ is 1 and $X^2$ is of the formula —(CH$_2$)$_{0-6}$—CH.

9. The method of claim 3 wherein $1^3$ is 0.

10. The method of claim 3 wherein $1^1$ and $1^2$ are 0.

11. The method of claim 3 wherein $n^1$ is 1 and $X^1$ represents a linker which spaces the benzhydril moiety from N at a distance of 3–20 Å.

12. The method of claim 11 wherein $n^1$ is 1 and $X^1$ contains at least one heteroatom selected from O and N.

13. The method of claim 11 wherein $n^1$ is 1 and $X^1$ represents —(CH$_2$)$_{1-8}$— or —(CH$_2$)$_{1-5}$—CH=CH—(CH$_2$)$_{0-3}$—.

14. The method of claim 1 wherein the compound of formula (1) is of the formula (1b)

(1b)

wherein Z is N or CH;

wherein each of $n^1$ and $n^2$ is independently 0 or 1;

$X^1$ and $X^2$ are linkers; and

Cy represents one or two substituted or unsubstituted aliphatic cyclic or heterocyclic moieties or consists of one substituted or unsubstituted aliphatic cyclic or heterocyclic moiety and one substituted or unsubstituted aromatic or hetroaromatic moiety.

15. The method of claim 14 wherein $n^2$ is 1 and $X^2$ represents a linker which spaces Cy from Z at a distance of 3–20 Å.

16. The method of claim 15 wherein $n^2$ is 1 and $X^2$ contains at least one heteroatom selected from N and O.

17. The method of claim 15 wherein $n^2$ is 1 and $X^2$ represents —(CH$_2$)$_{1-8}$— or —(CH$_2$)$_{1-5}$—CH=CH—(CH$_2$)$_{0-3}$—.

18. The method of claim 14 wherein $1^3$ is 0.

19. The method of claim 14 wherein $1^1$ and $1^2$ are 0.

20. The method of claim 14 wherein $n^1$ is 1 and $X^1$ represents a linker which spaces the benzhydril moiety from N at a distance of 3–20 Å.

21. The method of claim 20 wherein $n^1$ is 1 and $X^1$ contains at least one heteroatom selected from O and N.

22. The method of claim 20 wherein $n^1$ is 1 and $X^1$ represents —(CH$_2$)$_{1-8}$— or —(CH$_2$)$_{1-5}$—CH=CH—(CH$_2$)$_{0-3}$—.

23. A pharmaceutical composition for use in treating conditions characterized by aberrant N-type calcium channel activity which composition comprises, in admixture with a pharmaceutically acceptable excipient, a dosage amount effective to modulate N-type calcium channel activity of a compound of the formula (1)

wherein m is 0, 1 or 2;

wherein when m is 0, Z is O, when m is 1, Z is N, and when m is 2, Z is C;

Y is H, OH, NH$_2$, or an organic moiety of 1–20C, optionally additionally containing 1–8 heteroatoms selected from the group consisting of N, P, O, S and halo;

each $1^1$ and $1^2$ is independently 0–5;

$1^3$ is 0 or 1;

each of $R^1$, $R^2$ and $R^3$ is independently alkyl (1–6C), aryl (6–10C) or arylalkyl (7–16C) optionally containing

1–4 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1–4C) or alkyl (1–6C);

n is 0 or 1;

X is a linker;

with the proviso that Y is not a tropolone, a coumarin, or an antioxidant containing an aromatic group and with the fuirther proviso that if $1^3$ is 0, neither $R^1$ nor $R^2$ can be F in the para position.

24. A library comprising at least ten different compounds of the formula (1)

wherein m is 0, 1 or 2;

wherein when m is 0, Z is O, when m is 1, Z is N, and when m is 2, Z is C;

Y is H, OH, $NH_2$, or an organic moiety of 1–20C, optionally additionally containing 1–8 heteroatoms selected from the group consisting of N, P, O, S and halo;

each $1^1$ and $1^2$ is independently 0–5;

$1^3$ is 0 or 1;

each of $R^1$, $R^2$ and $R^3$ is independently alkyl (1–6C), aryl (6–10C) or arylalkyl (7–16C) optionally containing 1–4 heteroatoms selected from the group consisting of halo, N, P, O, and S or each of $R^1$ and $R^2$ may independently be halo, COOR, $CONR_2$, $CF_3$, CN or $NO_2$, wherein R is H or lower alkyl (1–4C) or alkyl (1–6C);

n is 0 or 1; and

X is a linker.

25. A method to identify a compound which antagonizes a target receptor which method comprises contacting host cells displaying said target receptor in the presence of an agonist for said receptor and with the members of the library of claim 14;

assessing the ability of the members of the library to affect the response of the receptor to its agonist; and identifyig as an antagonist any member of the library which diminishes the response of the receptor to its agonist.

26. The method of claim 25 wherein the receptor is an ion channel.

* * * * *